United States Patent [19]

Jochum et al.

[11] Patent Number: 5,086,148
[45] Date of Patent: Feb. 4, 1992

[54] POLYETHER-IMPRESSION MATERIAL AND METHOD FOR ITS PREPARATION AND USE

[75] Inventors: Peter Jochum; Oswald Gasser, both of Seefeld; Wolf-Dietrich Zahler, Seefeld-Hechendorf; Gunther Lechner, Frieding; Rainer Guggenberger, Hechendorf; Klaus Ellrich, Worthsee, all of Fed. Rep. of Germany

[73] Assignee: ESPE Stiftung & Co., Produktions - und Vertriebs KG, Seefeld, Fed. Rep. of Germany

[21] Appl. No.: 435,994

[22] Filed: Nov. 14, 1989

[30] Foreign Application Priority Data

Nov. 14, 1988 [DE] Fed. Rep. of Germany ....... 3838587

[51] Int. Cl.$^5$ .............................................. C08G 77/06
[52] U.S. Cl. ...................................... 528/15; 525/403; 525/478; 528/31; 528/32; 528/25
[58] Field of Search ...................... 528/32, 15, 31, 25; 525/403

[56] References Cited

U.S. PATENT DOCUMENTS 4,855,379  8/1989  Budnik et al. .................... 528/15
4,906,707  3/1990  Yukimoto et al. ................ 525/403

Primary Examiner—Melvyn I. Marquis
Attorney, Agent, or Firm—Birch, Stewart, Kolasch & Birch

[57] ABSTRACT

A polyether-impression material comprising components
(a) a polyether, which has at least two optionally substituted vinyl- and/or allyl-end groups,
(b) an SiH component,
(c) a platinum catalyst, and optionally
(d) the usual additives
characterized in that the SiH-component (b) can be obtained by the reaction of at least a bi- functional, or polyfunctional, e.g., trifunctional, allyl- or vinyl-hydrocarbon compound, the hydrocarbon radical of which, without taking account of the allyl- or vinyl-groups and the optionally present alkylene ether groups, has 6 to 30 C-atom and contains at least one aromatically unsaturated, heterocyclic, or cycloaliphatic ring, with at least one mole per vinyl- or allyl-group of at least a bifunctional, or polyfunctional, e.g., trifunctional, SiH compound of the formula:

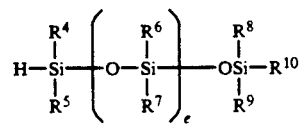

or

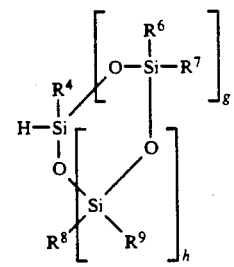

in which
e=0 to 8,
g=0 to 8,
h=0 to 4 and $R^4$ and $R^{10}$ are the same or different, and are each H, methyl or ethyl, with the proviso that at least 1 and at the most 5 of $R^4$ to $R^{10}$ are H, wherein g and h cannot simultaneously be O, and wherein at least the components (b) and (c) lie spatially separated from each other.

12 Claims, No Drawings

POLYETHER-IMPRESSION MATERIAL AND METHOD FOR ITS PREPARATION AND USE

BACKGROUND OF THE INVENTION

In the production of dentures in a dental laboratory, a "working model" which reproduces the teeth and jaw proportions of a patient as closely as possible is the most important prerequisite. For this purpose, a negative form is first produced by the dentist in the mouth of the patient using so-called impression materials. The initially plastic workable impression material is introduced into the patient's mouth on an impression plate and solidified as much as possible to an elastic material. This represents the negative form when removed. This mold could then be finally filled with model material, thus resulting in a working model.

DISCUSSION OF RELATED ART

Highly precise elastic impression materials, which are distinguished by high accuracy, high dimensional stability and good reproduction of detail, are for example, materials based on agar-agar, polysulphide, polyether or addition cross-linking silicones. Substances containing aziridine groups are polymerized to produce the polyether materials, such as those described in U.S. Pat. Nos. 3,453,242 and 4,093,555. Generally, in addition to the compounds containing aziridine groups, additives such as fillers, dyestuffs and further auxiliary agents are also used. Sulphonium salts, which are known from U.S. Pat. No. 4,167,618, are well suited to initiate the polymerization reactions.

As a result of their hydrophilic property, the polyether materials are ideal for recording at accurately as possible the teeth in a mouth, due to their good flowing characteristics even in a damp mouth environment.

The hardening of an addition cross-linking silicone impression material is achieved by a reaction of a polysiloxane having vinyl end groups with a polysiloxane having SiH end groups in the presence of certain platinum catalysts. The impressions obtained in this way are distinguished by being characterized with very good elastic properties and high storage stability. However, because of the hydrophobic nature of silicones, the accuracy of a reproduction can only be described as being good to a limited extent.

To improve the hydrophilic property of silicone impression materials, it has been proposed to add polyethoxylated oligo-siloxanes or perfluoro-alkane additives to the addition cross-linking silicone impression material (e.g., WO 87/03001 or EP-A 0 231 420). These additives do in fact produce an improved contact angle of a water droplet on the impression material This improved wettability, however, only occurs after a marked time delay. Thus, this improvement has only an unsatisfactory effect on the malleability of the material in the mouth.

In DE-A 37 41 575 impression materials with the capacity to harden are described. These materials also contain, in addition to unsaturated polyethers with terminal alkenyl radicals, the reaction products of such substituted polyether with oligosiloxane radicals having at least two SiH groups in the molecule and platinum catalysts as the main constituents. They can be used as dental impression materials and have good elastic and very hydrophilic properties. The described SiH components containing siloxanes are however difficult to isolate because of their strong tendency to cross-linkage even during preparation and the storage stability of the impression materials Containing these siloxanes is only limited for this reason.

OBJECT AND SUMMARY OF THE INVENTION

The object of the present invention is to produce an elastic and storage-stable addition cross-linking polyether impression material.

This can be achieved by a polyether impression material comprising
(a) a polyether, which has at least two, optionally substituted vinyl- and/or allyl-end groups,
(b) a SiH component,
(c) a platinum catalyst and optionally
(d) the usual additives characterized in that the SiH-component (b) can be obtained by the reaction of at least a bifunctional, or polyfunctional, e.g., trifunctional, allyl- or vinyl-hydrocarbon compound, the hydrocarbon radical of which, without taking account of the allyl or vinyl groups and alkylene ether groups optionally present, has 6 to 30 carbon atoms and which contains at least one aromatically unsaturated, heterocyclic or cycloaliphatic ring, with at least one mole per vinyl or allyl group of at least a bi-functional, or polyfunctional, e.g., trifunctional, SiH compound, of the formulae

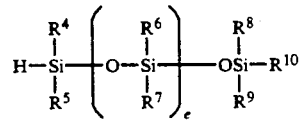

or

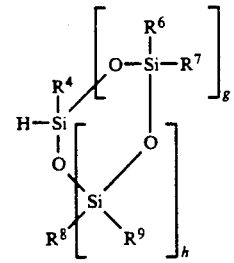

in which
e=0 to 8,
g=0 to 8,
h=0 to 4 and
$R^4$ to $R^{10}$ are the same or different, and are each H, methyl or ethyl, with the proviso that at least 1 and at the most 5 of $R^4$ to $R^{10}$ are H, wherein g and h cannot simultaneously be O, and wherein at least the components (b) and (c) are spatially separated from each other.

The impression material according to the invention is advantageous in that the SiH component contained therein does not have a tendency to crosslink and therefore is characterized with having a satisfactory storage stability.

Furthermore, in comparison to the impression material known from DE-A 37 41 575, it has more balances hydrophilic properties, in that on the one hand it is easily wettable by water and therefor has a good flow characteristic, and on the other hand, however, in the presence of water it has only a slight tendency to swell, i.e., the dimension stability is retained.

Preferably the allyl- or vinyl-hydrocarbon compound is an allylether-, vinylether-, allylester-, or vinylester-hydrocarbon compound.

As component (b), SiH-compounds of the formula:

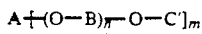

are preferably used,
wherein
A is a straight-chain or branched 2- to 6-valent hydrocarbon radical with 6 to 30 carbon atoms, containing at least one aromatically unsaturated or cycloaliphatic ring,
B is a straight-chain or branched saturated hydrocarbon radical with 2 to 6 carbon atoms,
m = 2 to 6,
n = 0 to 25 and
C' represents the radical

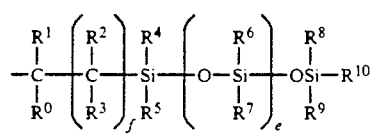

or

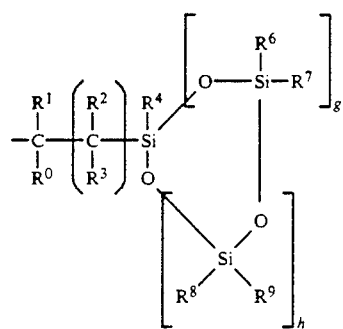

in which
$R^0$ to $R^3$ are the same or different, and are each H, methyl or ethyl, f is 1 or 2, and e, g, h, and $R^4$ to $R^{10}$ have the above meanings.

The polyether-impression material according to the invention Can be produced in such a way, that all components (a), (b) and (c) lie spatially separated from each other. However, the components (a) and (c) can also be mixed together with component (b) being kept apart. In another embodiment, part of component (a) can be mixed with component (c) and separate therefrom the remaining part of component (a) can be mixed with the component (b) and both part-mixtures kept spatially separated from each other. Shortly before using the impression material the individual components or part-mixtures can then be combined together and thoroughly mixed.

Another object of the invention is to use the above named addition cross-linking polyetherimpression material for the production of dimensionally stable dental impressions.

The di- or poly-allylethers of poly-ether-di or -polyols can be used, for example, as the unsaturated polyether (a). Ethylene-and propyleneoxide polymers, ethylene and propyleneoxide Co polymers as well as ethylene oxide- and tetrahydrofuran co-polymers can be used, for example, as the middle polyether unit. The polyetherdiols obtained therefrom can be reacted in a manner known per se, e.g., with allyl- or vinylchloride to form the unsaturated polyethers (a). The unsaturated polyethers preferably have average molecular weights of 1000 to 20,000, particularly preferred are from 1500 to 10,000 and most particularly preferred are from 2000 to 7000. Suitable unsaturated polyethers are described in the aforementioned DE-A 37 41 575, the disclosure of which to this extent is to be included herein.

Component (b) of the impression material according to the invention is an aromatic or cycloaliphatic compound substituted by siloxane radicals. In the above formula for the SiH compound the radical A is preferably a bivalent 1,4-phenylene-, 2,7-naphthylene-, 4,4'-isopropylidenediphenylene-, 4,4,'-biphenylylene-, phthaloyl-, terephthaloyl- or tricyclo-[5.2.1.0$^{2,6}$]-decan-3,8-dimethyl radical.

The radical B is preferably an ethylene or a propylene radical, m is preferably from 2 to 4 and especially preferred is 2, n is preferably from 0 to 10, and more particularly from 0 to 3.

In the radical C', the radicals $R^0$ to $R^3$ are preferably H or methyl, H in particular being preferred, and the radicals are the same, f is preferably 2, $R^4$ and $R^5$ are preferably methyl, $R^6$ is preferably H, $R^7$ and $R^9$ are preferably methyl, $R^8$ and $R^{10}$ are preferably H, e is preferably 0 to 5, and more particularly, 1 to 3, g is preferably 1 to 4 and h is preferably 1 to 2. Radical C' of the following formulae are particularly preferred:

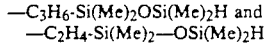
and

Compounds of the following formulae:

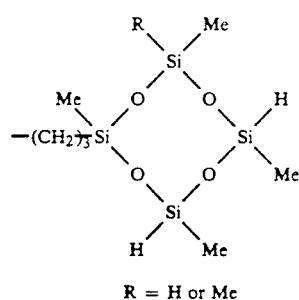

R = H or Me

The reaction products from triallyl-triazine-trione with at least three times the molecular quantity of at least a bifunctional, or polyfunctional, e.g., trifunctional SiH-compound of the formula above are for example well suited.

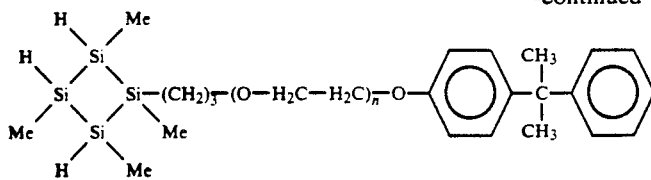 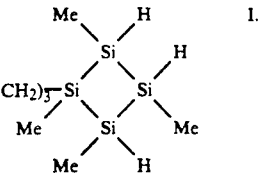

and

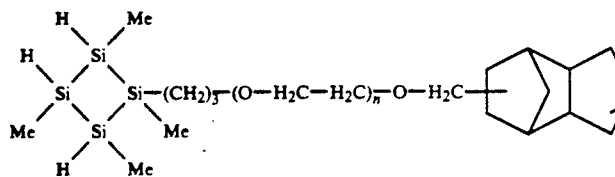 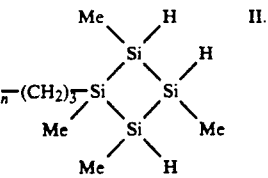

in which n is 0, 1, 2 or 3, are particularly preferred.

The siloxane-substituted aromatic or cycloaliphatic compounds can be produced according to the usual methods or as in DE-OS 37 41 575. They can be produced by reacting a di- or poly-allyl or -vinyl aromatic compound with a polyorganosiloxane, which contains at least two SiH groups, using a platinum catalyst in a mole ratio of at least two SiH groups to one allyl- or vinyl-group. Suitable starting substances are for example the diallylether of bisphenol A, of ethoxylated bisphenol A and of bishydroxymethyl-tricyclo-[5.2.1.0$^{2,6}$]-decan as well as phthalic and terephtalic acid diallyl ester. The catalyst used must be removed to produce storage-stable pastes. This can suitably be achieved by the adsorption of the catalyst with silica gel, kieselguhr or the like.

All catalyst which initiate hydrosilylation can be used as catalyst (c). For example, finely dispersed platinum, chloroplatinic acid or platinum complexes are suitable. Also suitable are all other compounds, which are known in the preparation of addition cross-linking silicones. Suitable platinum complexes are platinum olefin complexes, e.g., the reaction product of chloroplatinic acid with a polysiloxane containing at least one vinyl group.

The mole ratio of component (a) to component (b) is usefully chosen, such that per 1 mole of unsaturated radical, 1 to 10 moles of SiH-groups, preferably 1.5 to 3 moles of SiH-groups are present.

The quantity of the platinum catalyst (c) used, preferably amounts to 0.1 ppm to 5000 ppm, in particular 0.1 to 1000 μm, based on the total weight of the components (a) and (b).

To set the working conditions, in particular the flowability any hardness of the finished molding, the impression material optionally contains the usual inorganic and/or organic fillers. Suitable inorganic fillers are for example pyrogenic silicium dioxide, kieselguhr, silica gel, quartz powder, ground fibre-glass, titanium dioxide, aluminum oxide, magnesium oxide, calcium carbonate and mica. The particle-size distribution of the fillers used is preferably Chosen in such a way that no fillers with a particle size >50 μm are contained the maximum particle size preferably to 25 μm and more preferably to 5 μm. According to the intended use the quantity of filler amounts 0 to 80% by weight, preferably 5 to 50% by weight, and is based on the total weight of the molding material.

The fillers can be coated. Fillers coated with silane are preferred. The silanes known to be used for the coating of fillers can be used as the silane. Particularly suitable are, for example, hexamethyl-disilazane and divinyl-tetramethyldisilazane.

Furthermore, the mixtures according to the invention can contain additives such as plasticizers, pigments, anti-oxidating agents, release agents among others. Compounds such as tributylcitrate, dibenzyltoluene, polyethylene oxide as well as ethylene oxide copolymers and propylene oxide co-polymers are suitable as plasticizers. The quantity of plasticizer preferably amounts to 0 to 40 % by weight, and in particular 0 to 20 % by weight, referred to the total mass.

As the number of SiH group needed to guarantee rapid hardening is relatively large in relation to the quantity of unsaturated radicals in the hardenable molding material, during the hardening hydrogen gas can be liberated as a by-product. In order that this does not influence the dimensional stability, an absorber for the hydrogen gas is preferably introduced. Metal powders from pallatium, platinum, nickel, magnesium or zinc are suitable; especially suitable are carrier materials provided with these metals for example, palladiumcoated silica gel or palladium-coated calcium carbonate.

1ST EXAMPLE OF PREPARATION 7 mg of hexachloroplatinic acid is introduced into 7.92 g of (20 mmole) bisphenol-A bisallyloxyethylether and the mixture is stirred for 15 minutes at ambient temperature, until the majority of the hexachloroplatinic acid has dissolved. Following this 9.6 g of (40 mmole) tetramethylcyclotetrasiloxane is slowly added dropwise at ambient temperature. Within 20 minutes the temperature of the mixture rises to 55° C. Stirring is continued until the mixture has cooled to a temperature of 30° C. and is then continued for an additional 2 hours Finally, filtration with silica gel removes a small amount of a black precipitate and 10 g of compound 1 is obtained.

EXAMPLE 1

1 g of diallylether of a polypropylene glycol with an average molecular weight of 2000 and 0.2 g of a platinum catalyst solution, comprising 0.1% of hexachloroplatinic acid in divinyltetramethyldisiloxane, are introduced into 0.27 g of compound 1 and the mixture obtained is stirred. After approximately 2½ minutes setting begins and is completed after approximately 6 minutes.

A solid rubber is obtained, which has very good elastic properties and exceptional tensile strength.

The impression material can be easily wetted with water before and after setting, without absorbing any significant amount of water.

2ND EXAMPLE OF PREPARATION

As described in the example of preparation 1, 20 mmoles of each of the diallyl compounds listed in Table 1 below with respectively 7 mg of hexachloroplatinic acid and 9.6 g of tetramethylcyclotetrasiloxane is reacted to yield the respective SiH compounds listed in Table 1 below. The characterization of the products is carried out by their FTIR-spectrum. The SiH oscillation of the tetramethylcyclotetrasiloxane adduct can be seen at 2173 cm$^{-1}$. The wave numbers of the SiH compound according to the invention are provided in Table 1 below. The completeness of the reaction can be easily followed by NMR-spectroscopy. The wide multiplet of the allyl group at 5.0 to 6.3 ppm disappears on Completion of the reaction.

TABLE 1

| Allyl compound | Quantity (g) | Yield of SiH compound (g) | IR spectrum of the SiH compound (SiH oscillation) |
|---|---|---|---|
| 4,4'-bis-(allyloxy-ethyl-ethoxy)-2,2-diphenylpropane | 13.4 | 18 | 2171 cm$^{-1}$ |
| 4,4'-bis-(allyloxy)-2,2-diphenyl-propane | 6.16 | 6.5 | 2168 cm$^{-1}$ |
| phthalic acid diallyl ester | 4.93 | 11 | 2168 cm$^{-1}$ |

EXAMPLE 2

The compounds obtained according to the second example of preparation, as described in Example 1, were reacted with polypropylene glycol diallylether with an average molecular weight of 2000 and the platinum catalyst, containing 0.1% by weight of hexachloroplatinic acid in divinyltetramethyldisiloxane. In each case hardening begins after 2½ minutes and is complete after approximately 6 minutes. The rubber obtained have excellent tensile strengths and elasticities.

The impression material is easily wettable with water both before and after hardening, without taking up any significant amount of water.

EXAMPLE 3

A homogeneous solution is obtained from 2.3 g of H$_2$PtCl$_6$×6H$_2$O and 11.5 g of tributylcitrate by stirring at 100° C. for 5 minutes. This solution is allowed to cool to 50° C. and 13.8 parts by weight of divinyltetramethyldisiloxane is added, then the solution is heated to 100° again and stirred for a further 5 minutes at 100° C. After cooling to ambient temperature a clear catalyst solution is obtained. 0.01 parts by weight of this catalyst solution is kneaded with 2 parts by weight of polypropyleneglycol diallylether with an average molecular weight of 2000 and 0.02 parts by weight of palladium on calcium carbonate and 0.9 parts by weight of a pyrogenic silane coated to a stable catalyst paste.

0.64 parts by weight of the diallyl ether described above are kneaded with 0.47 parts by weight of the reaction product described in Example of Preparation 2 of tetramethylcyclotetrasiloxane and 4,4-bis-(allyloxy)-2,2-diphenylpropane as well as 1.9 parts by weight of a calcium carbonate coated with stearic acid to a stable basic paste.

The catalyst paste and the basic paste are mixed together in equal parts by weight. After 2 minutes 45 seconds hardening begins and is complete after approximately 8 minutes. The freshly mixed paste has an excellent stability, it does not run off the impression plate, but can however easily be applied around the teeth with an elastomer injection for dental impressions. After 30 minutes the material has a Shore hardness A of 43, the elastic deformation amounts to 8% after 60 minutes and the remaining deformation to 0.5% after 60 minutes. (The measured values were determined according to ADA 19 for dental molding compounds). The molding material can easily be wet with water both before and after hardening without any swelling due to water absorption.

What is claimed is:

1. A polyether-impression material comprising
   (a) a polyether, which has at least two, substituted or non-substituted vinyl- and/or allyl end groups,
   (b) a SiH component and
   (c) a platinum catalyst
characterized in that the SiH component (b) is obtained by the reaction in the presence of a platinum catalyst of at least a bifunctional, or polyfunctional hydrocarbon compound, the hydrocarbon radical of which, without taking account of the allyl or vinyl groups and the optionally present alkylene ether groups has 6–30 carbon atoms and contains at least one aromatically unsaturated, heterocyclic, or cycloaliphatic ring, with at least one mole per vinyl- or allyl group of at least a bifunctional, or polyfunctional SiH-compound of the formulae

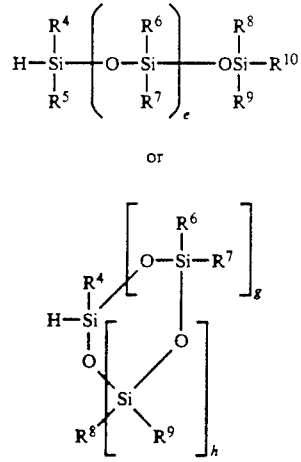

or in which
e = 0 to 8,
g = 0 to 8,
h = 0 to 4 and

R$^4$ to R$^{10}$, are the same or different, and are each H, methyl or ethyl, with the proviso that at least 1 and at most 5 of R$^4$ to R$^{10}$ are H, wherein g and h cannot simultaneously be 0, and wherein at least the components (b) and (c) are spatially separated from each other.

2. The polyether-impression material according to claim 1, characterized in that the bifunctional, or polyfunctional hydrocarbon compound is an allyether-, vinylether-, allylester-, or vinylester-hydrocarbon compound.

3. The polyether-impression material according to claim 1, characterized in that the component (b) is a SiH-compound of the formula

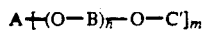

in which
A is a straight-chain or branched 2- to 6-valent hydrocarbon radical with 6 to 30 C-atoms, containing at least one aromatically unsaturated or cycloaliphatic ring,
B is a straight-chain or branched saturated hydrocarbon radical with 2 to 6 carbon atoms,
m=2 to 6,
n=0 to 25, and
C' represents the radical

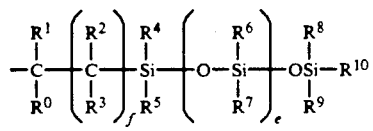

or

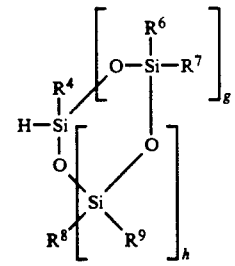

in which
$R^0$ to $R^3$ are the same or different, and are each H, methyl or ethyl,
e=0 to 8,
f=1 or 2,
g=0 to 8,
h=0 to 4 and
$R^4$ to $R_{10}$, are the same or different, and are each H, methyl or ethyl, with the proviso that at least 1 and at most 5 of $R^4$ to $R^{10}$ are H, wherein g and h cannot simultaneously be 0, and wherein at least the component (b) and (c) are spatially separated from each other.

4. The polyether-impression material according to claim 1, characterized in that said hydrocarbon radical is a bivalent 1,4-phenylene-, 2,7-naphthylene-, 4,4'-isopropylidene-diphenylene-, 4,4'-biphenylylene-, phthaloyl-, terephthaloyl- or tricyclo-[5.2.1.1$^{2,6}$]-decan-3,8-dimethylene radical.

5. The polyether-impression material according to claim 1, characterized in that the mole ratio of component (a) to component (b) is per 1 mole of unsaturated radical of polyether (a) there is 1 to 10 moles of the SiH groups of SiH component (b).

6. The polyether-impression material according to claim 1, characterized in that platinum catalyst (c) is present in the form of finely dispersed platinum, chloroplatinic acid or platinum complexes.

7. The polyether-impression material according to claim 1, characterized in that the quantity of platinum catalyst (c) amounts to 0.1 ppm to 5000 ppm, based on the total weight of components (a) and (b).

8. The polyether-impression material according to claim 1, characterized in that the mole ratio of component (a) to component (b) is per 1 mole of unsaturated radical of polyether (a) there is 1.5 to 3 moles of the SiH groups of SiH component (b).

9. The polyether-impression material according to claim 1, characterized in that the quantity of platinum catalyst (c) amounts to 0.1 ppm to 1000 ppm, based on the total weight of components (a) and (b).

10. A process for the preparation of a polyether-impression material comprising
(a) a polyether, which has at least two, substituted or nonsubstituted vinyl- and/or allyl end groups,
(b) a SiH component and
(c) a platinum catalyst
characterized in that the SiH component (b) is obtained by the reaction in the presence of a platinum catalyst of at least a bifunctional, or polyfunctional hydrocarbon compound, the hydrocarbon radical of which, without taking account of the allyl or vinyl groups and the optionally present alkylene ether groups has 6–30 carbon atoms and contains at least one aromatically unsaturated, heterocyclic, or cycloaliphatic ring, with at least one mole per vinyl- or allyl group of at least a bifunctional, or polyfunctional SiH-compound of the formulae

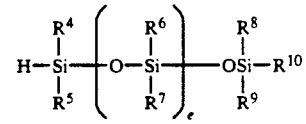

or

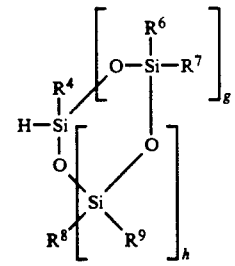

in which
e=0 to 8,
e=0 to 8,
h=0 to 4 and
$R^4$ to $R^{10}$, are the same or different, and are each H, methyl or ethyl, with the proviso that at least 1 and at most 5 of $R^4$ to $R^{10}$ are H, wherein g and h cannot simultaneously be 0, and wherein at least the components (b) and (c) are spatially separated from each other, characterized in that component (a) and component (c) are mixed together and component (b) is spatially separated from the mixture.

11. A process for the preparation of a polyether-impression material comprising (a) a polyether, which has at least two, substituted or non-substituted vinyl- and/or allyl end group, (b) a SiH component and (c) a platinum catalyst characterized in that the SiH component (b) is obtained by the reaction in the presence of a platinum catalyst of at least a bifunctional, or polyfunctional hydrocarbon compound, the hydrocarbon radical of which, without taking account of the allyl or vinyl groups and the optionally present alkylene ether groups has 6–30 carbon atoms and contains at least one aromatically unsaturated, heterocyclic, or cycloaliphatic ring, with at least one moler per vinyl- or allyl group of at least a bifunctional, or polyfunctional SiH-compound of the formulae

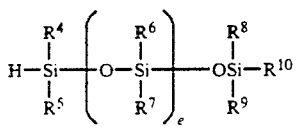

or

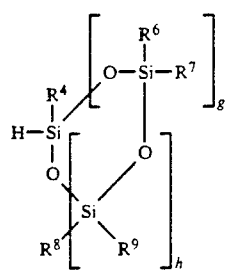

in which $e = 0$ to 8, $g = 0$ to 8, $h = 0$ to 4 and $R^4$ to $R^{10}$, and the same or different, and are each H, methyl or ethyl, with the proviso that at least 1 and at most 5 of $R^4$ to $R^{10}$ are H, wherein q and h cannot simultaneously be 0, and wherein at least the components (b) and (c) are spatially separated from each other, characterized in that a part of component (a) is mixed with component (c) and the remaining part of component (a) is mixed with component (b) and both part-mixtures are kept spatially separated from each other.

12. A polyether-impression material comprising (a) a polyether, which has at least two, substituted or non-substituted vinyl- and/or allyl end groups, (b) a SiH component, characterized in that the component (b) is a SiH-compound of the formula

in which

A is a bivalent 1,4-phenylene-, 2,7-naphthylene-, 4,40-isopropylidene-diphenylene-, 4,4′-biphenylylene-, phthaloyl-, terephthaloyl- or tricyclo-[5.2.1.0$^{2,6}$]-decan-3,8-dimethylene radical, B is a straight-chain or branched saturated hydrocarbon radical with 2 to 6 carbon atoms, $m = 2$ to 6, $n = 0$ to 25, and c′ represents the radical

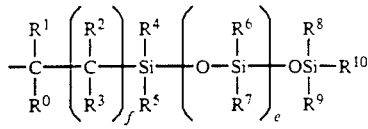

or

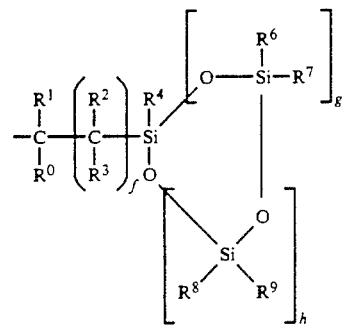

in which $R^0$ to $R^3$ are the same or different, and are each H, methyl or ethyl, $e = 0$ to 8, $f = 1$ or 2, $g = 0$ to 8, $h = 0$ to 4 and $R^4$ to $R^{10}$, are the same or different, and are each H, methyl or ethyl, with the proviso that at least 1 and at most 5 of $R^4$ to $R^{10}$ are H, wherein g and h cannot simultaneously be 0, and wherein at least the components (b) and (c) are spatially separated from each other, and (c) a platinum catalyst, characterized in that the SiH component (b) is obtained by the reaction in the presence of a platinum catalyst of at least a bifunctional, or polyfunctional hydrocarbon compound, the hydrocarbon radical of which, without taking account of the allyl or vinyl groups and the optionally present alkylene ether groups has 6–30 carbon atoms and contains at least one aromatically unsaturated, heterocyclic, or cycloaliphatic ring, with at least one mole per vinyl- or allyl group of at least a bifunctional, or polyfunctional SiH-compound of the formulae

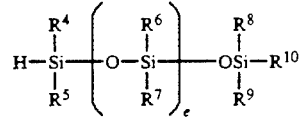

or

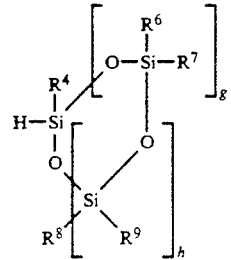

in which e=0 to 8,
g=0 to 8,
h=0 to 4 and
$R^4$ to $R^{10}$, are the same or different, and are each H, methyl or ethyl, with the proviso that at least 1 and at most 5 of $R^4$ to $R^{10}$ are H, wherein g and h cannot simultaneously be 0, and wherein at least the components (b) and (c) are spatially separated from each other.

* * * * *